United States Patent [19]

Kurath

[11] 4,338,307
[45] Jul. 6, 1982

[54] 2'-N-DES-β-LYSYL ANTIBIOTIC AX-127B-1 AND 4-N-ACYL AND ALKYL DERIVATIVES THEREOF

[75] Inventor: Paul Kurath, Waukegan, Ill.

[73] Assignee: Abbott Laboratories, North Chicago, Ill.

[21] Appl. No.: 205,813

[22] Filed: Nov. 10, 1980

[51] Int. Cl.³ .................... A61K 31/71; C07H 15/22
[52] U.S. Cl. .................................. 424/180; 424/181; 435/80; 536/16.8
[58] Field of Search ............. 424/180, 181; 536/17 B, 536/17 R

[56] References Cited

U.S. PATENT DOCUMENTS 4,091,032 5/1978 Tadanier et al. ............. 536/17 R
4,187,299 2/1980 Post .............................. 536/17 R
4,241,182 12/1980 Takasawa et al. ............ 536/17 R
4,283,529 8/1981 Rosenbrook, Jr. ............ 536/17 R

OTHER PUBLICATIONS

Tadanier et al., "Carbohydrate Research", vol. 79, pp. 91–102, vol. 85, pp. 61–71, 1980.

Primary Examiner—Johnnie R. Brown
Attorney, Agent, or Firm—Joyce R. Niblack; Gildo E. Fato; Dennis K. Shelton

[57] ABSTRACT

2'-N-Des-β-lysyl antibiotic AX-127B-1 and the 4-N-acyl and alkyl derivatives thereof. The compounds are useful as intermediates in the preparation of 3-O-demethyl antibiotic AX-127B-1 and its derivatives. 2'-N-des-β-lysyl antibiotic AX-127B-1 is also useful as a broad spectrum antibacterial agent.

15 Claims, No Drawings

2'-N-DES-β-LYSYL ANTIBIOTIC AX-127B-1 AND 4-N-ACYL AND ALKYL DERIVATIVES THEREOF

BACKGROUND OF THE INVENTION

Antibiotic AX-127B-1 is a relatively new aminoglycoside antibiotic. (Commonly assigned, co-pending U.S. Ser. No. 008,378, filed Feb. 1, 1979).

Chemical modification of the aminoglycoside antibiotics, as with other classes of antibiotics, has been found to improve the activity, either intrinsic or against resistant strains of organisms, or to reduce the toxicity of the parent antibiotics. And, because of the development of aminoglycoside-resistant strains and inactivation of the parent antibiotics by R-mediated factors which can develop, the search continues for new entities which are either superior to known aminoglycosides or which provide an alternative therapy when resistant organisms develop.

In a related family of aminoglycoside antibiotics, the fortimicins, 3-O-demethylation has been found to improve the intrinsic activity of the antibiotics. See, for example, U.S. Pat. No. 4,124,756.

3-O-demethyl-antibiotic AX-127B-1 and its 4-N-alkyl and acyl derivatives are disclosed and claimed in commonly assigned, copending U.S. Ser. No. 126,732, filed Mar. 3, 1980, now U.S. Pat. No. 4,283,529. The present invention provides derivatives of antibiotic AX-127B-1 which are useful as intermediates in the preparation of the 3-O-demethyl derivatives of AX-127B-1, and, in some instances, are also useful as antibiotics and antibacterial agents.

SUMMARY

The present invention provides 2'-N-des-β-lysyl antibiotic AX-127B-1 and the 4-N-acyl and alkyl derivatives thereof. The compounds are useful as intermediates in the preparation of 3-O-demethyl derivatives of AX-127B-1.

DETAILED DESCRIPTION OF PREFERRED EMBODIMENTS

Antibiotic AX-127B-1 is represented by the formula:

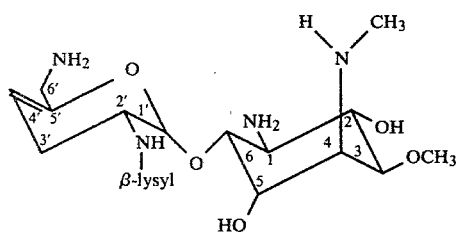

The 2'-N-des-β-lysyl derivatives of AX-127B-1 of this invention are represented by the formula:

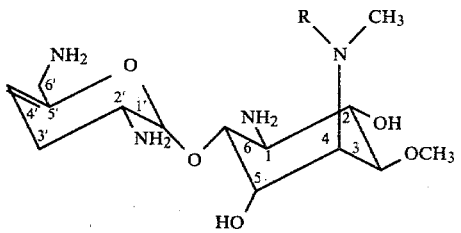

wherein R is selected from the group consisting of hydrogen, acyl, aminoacyl, diaminoacyl, N-loweralkylaminoacyl, N,N-diloweralkylaminoacyl, hydroxy-substituted aminoacyl, loweralkyl, aminoloweralkyl, diaminoloweralkyl, hydroxyloweralkyl, N-loweralkylaminoloweralkyl, N,N-diloweralkylaminoloweralkyl, N-loweralkylaminohydroxyloweralkyl, and N,N-diloweralkylaminohydroxyloweralkyl, and the pharmaceutically acceptable salts thereof.

The term "acyl", as used herein, refers to acyl radicals of loweralkylcarboxylic acids represented by the formula —COR wherein R is loweralkyl, i.e. acetyl, propionyl, butyryl, valeryl, etc.

The terms aminoacyl, hydroxy-substituted aminoacyl, etc. include, but are not limited to naturally occuring amino acids such as glycyl, valyl, alanyl, sarcosyl, lysyl, leucyl, prolyl, seryl, and the like as well as groups such as 2-hydroxy-4-aminobutyryl and the like. The amino acid residues, with the exception of glycyl, beta-alanyl and other non-asymetric amino acids residues, can be either in the D or L configuration or mixtures thereof.

The term "loweralkyl", as used herein, refers to straight or branched chain alkyl radicals containing from 1 to 6 carbon atoms, inclusive, and includes, but is not limited to methyl, ethyl, n-propyl, iso-propyl, n-butyl, iso-butyl, tert-butyl, n-pentyl, 1-methylbutyl, 2,2-dimethylpropyl, n-hexyl, 2-methylpentyl and the like.

The substituted amino groups are well known in the art and include, for example, beta-aminoethyl, N-methylaminoethyl, N,N-dimethylaminopropyl, hydroxyethyl, 2-hydroxy-4-aminobutyl, and the like.

The term "pharmaceutically acceptable salts" refer to the non-toxic acid addition salts which can be prepared either in situ during the final isolation and purification or by separately reacting the free base with a suitable organic or inorganic acid by methods well know in the art. Representative salts include the mono or per salts such as the hydrochloride, hydrobromide, sulfate, bisulfate, tetrahydrochloride, acetate, oxalate, valerate, oleate, palmitate, stearate, laurate, borate benzoate, lactate, phosphate, tosylate, citrate, maleate, fumarate, succinate, tartate, napsylate, and the like. 2'-N-Des-β-lysyl-antibiotic AX-127-B-1, in addition to its use as a valuable intermediate in the preparation of 3-O-demethyl-AX-127B-1 and its 4-N-acyl and alkyl derivatives, is useful as an antibacterial agent against susceptible strains of gram negative and gram positive bacilli such as *Staphylococcus aureus, Escherichia coli, Psuedomonas aeruginosa, Bacillus subtilis, Proteus vulgaris, Shigella sonnei, Salmonella typhi,* and *Klebsiella pneumoniae.* The antibiotic shows improved activity over Fortimicin A against *Psuedomonas aeruginosa* 27853 and Fortimicin B against a broad spectrum of bacilli.

The term "susceptible strains" refers to strains of bacilli or organisms which have been demonstrated to be sensitive to a particular antibiotic in a standard in vitro sensitivity test and thus in vitro activity has been established for a particular antibiotic against a specific strain of a particular organism.

The antibiotic of this invention is administered parenterally, i.e., intravenously, intramuscularly, intraperitoneally, or subcutaneously for systemic effect in daily dosages of from about 30 to about 120 mg/kg of body weight daily, preferably from about 50 to 80 mg/kg daily, based on lean body weight. It is further preferred to administer the antibiotic in divided daily dosages. Oral administration to sterilize the intestinal tract is also contemplated by the present invention.

The compounds of this invention can be O-demethylated to provide the O-demethyl derivatives of antibiotic AX-127B-1 by dissolving the compound to be O-demethylated in, for example, methylene chloride, cooling the reaction mixture to a temperature of from about $-72°C$. to about $30°$ C., preferably about $0°$ C., and treating the reaction mixture with from about 10 to about 100 equivalents of a boron trihalide, preferably boron tribromide, with stirring, for about 10 to about 60 minutes at temperatures of between $-72°$ C. to $100°$ C., preferably from about $-4°$ C. to about $38°$ C. Solvent and residual boron trihalide are removed in vacuo, the reaction mixture is treated with an appropriate solvent such as methanol to remove residual solvent and boron trihalide and evaporated to a residue to provide the desired derivative.

The following examples further illustrate the present invention:

EXAMPLE 1

Culture AB-127B-46 was maintained on ATCC medium #172 agar slants consisting of 1% glucose, 2% soluble starch, 0.5% Difco yeast extract, 0.5% N-Z amine type A (Sheffield Chemical Co.), 0.1% $CaCO_3$, 1.5% agar, and distilled water QS to 1 liter.

First passage inoculum seed tubes (25×150 mm) containing 10 ml. of sterile S-3 seed medium (Table 1) and closed with Bellco stainless steel caps were inoculated with a sterile loop from ATCC medium #172 agar slant cultures of AB-127B-46. Seed tubes were incubated on a rotary shaker (250 r.p.m.) at 30° C. for 96 hours. At that time 5% vegetative inoculum from the first passage seed tube was transferred aseptically to 500 ml. Erlenmeyer flasks containing 100 ml. of sterile S-3 seed medium and closed with cotton plugs. Inoculated second passage seed flasks were then incubated on a rotary shaker (250 r.p.m.) at 30° C. for 72 hours. Antibiotic production fermentation flasks (500 ml. Erlenmeyer) containing 100 ml. of sterile AF1b medium (Table 1) and closed with cotton plugs were inoculated with 5% vegetable inoculum from the second passage seed flasks.

The inoculated AF1b antibiotic production medium flasks were then incubated on a rotary shaker (250 r.p.m.) at 30° C. for 5 to 7 days and then harvested.

The harvested whole culture fermentation beer from a series of flasks was pooled (30 liters), adjusted to pH 2 with sulfuric acid and clarified by centrifugation or by filtration through celite. The clarified fermentation liquor was then poured into a 6.5 cm. diameter glass column containing 0.7 liters of AMBERLITE IRC 84 cation exchange resin (ammonia form). The active antibiotic was absorbed on the resin and the effluent beer was discarded. The resin column was washed thoroughly with water. Antibiotic activity was then eluted with 1 N aqueous ammonia. Active fractions were determined by dipping paper discs in eluate fractions and testing for activity on agar plates seeded with *Staphylococcus aureus* ATCC 6538P. Active fractions were combined and concentrated to remove excess ammonia and were then neutralized to pH 6.5 with sulfuric acid. The concentrate was then passed through a glass column containing REXYN 102 ($NH_4+$) 2 cm. diameter×6 cm. in height or 18 ml. of resin. The column was washed with water and then eluted by stepwise gradient with aqueous ammonia starting with 0.05 N and increasing to 1 N ammonia.

Active fractions were again located by the paper disc method and further examined by both paper chromatography and thin-layer chromatography as previously described. Active fractions containing the antibiotic described in this invention were combined, concentrated to remove excess ammonia, neutralized to pH 6.5 with sulfuric acid and reduced to dryness under vacuum. The sulfate salt of the antibiotic was dissolved in distilled water and converted to free base by passing through a small glass column containing DOWEX 1-X2 ($OH^-$).

TABLE 1

| Ingredient | gm/liter |
|---|---|
| S-3 Seed Medium | |
| Staclipse J soluble starch (Staley) | 24 |
| glucose monohydrate | 1 |
| yeast extract (Difco) | 5 |
| tryptone (Difco) | 5 |
| beef extract (Wilson) | 3 |
| $CaCO_3$ | 4 |
| tap water QS to 1.0 liter | |
| sterilization: 30 min., 121° C. at 15-16 lb. pressure | |
| AF1b Fermentation Medium | |
| glucose monohydrate | 10 |
| peptone (Difco) | 5 |
| yeast extract (Difco) | 5 |
| $CaCO_3$ | 1 |
| pH 7.3 | |
| tap water QS to 1.0 liter | |
| sterilization: 30 min., 121° C. at 15-16 lb. pressure | |

EXAMPLE 2

Culture AB-127B-46 was inoculated into first passage 500 ml. Erlenmeyer seed flasks containing 100 ml. of sterile S-3 seed medium and closed with cotton plugs. Inoculated flasks were incubated on a rotary shaker (250 r.p.m.) at 30° C. for 96 hours. At that time, 5% vegetative inoculum was transferred into similar 500 ml. Erlenmeyer flasks containing 100 ml. of sterile S-3 seed medium. Inoculated second passage seed flasks were incubated on a rotary shaker at 30° C. for 72 hours. Second passage seed flasks were used to inoculate a series of 30 liter stainless steel fermentors at a level of 5% inoculum. Fermentation conditions for 30 liter fermentors were as follows:

| | |
|---|---|
| Fermentation Medium: | AF1b (see Table 5) |
| Fermentor Volume: | 12 liters |
| Sterilization Time: | 1 hr., 121° C., 15-16 lb pressure |
| Antifoam: | .01% P-2000 polyethylene glycol (Dow Chemical Co.) |
| Incubation Temp.: | 30° C. |
| Agitation: | 250 r.p.m. |
| Impeller Blade Angle: | 45° |
| Air Rate: | 1 volume/volume/min. |

Fermentors were incubated for 5 days and then harvested. The desired antibiotic described in this invention was isolated and purified as described in the Example 1.

EXAMPLE 3

2'-N-Des-β-lysyl-antibiotic AX-127B-1

A total of 4.66 g of the sulfate salt of antibiotic AX-127-B1 sulfate salt (prepared according to U.S. Ser. No. 008,378, filed Feb. 1, 1979) was converted to the free base by treatment with AG 2×8 resin (OH$^-$) form, BioRad Laboratories, to afford 2.71 g of the free base after lyophilization. Raman spectrum $v_{max}$ 1690$^{-1}$. The later was refluxed gently in 25 ml of hydrazine hydrate for 22 hours. Evaporation of the hyrdrazine left a residue of 2.755 g of crude product. The crude product was chromatographed on 140 g of silica gel in the lower phase of methanol-methylene chloride-ammonium hydroxide[1:1:1(v/v/v)]. Ten ml fractions were collected and a total of 1.325 g of product obtained.

4-N-Acyl derivatives of 2'-N-des-β-lysyl antibiotic AX-127B-1 are readily prepared by reacting 2'-N-des-β-lysyl AX-127B-1 with o-nitro(benzyloxycarbonyloxy)succinimide to afford the 1,2',6'-tri-o-nitrobenzyloxycarbonyl intermediate according to the procedure set for in U.S. Pat. No. 4,091,032. The product formed in the above reaction is isolated by column chromatography and 4-N-acylated by treatment with, for example, azide coupling by reaction of a suitably N-protected (e.g. o-nitrobenzyloxycarbonyl)amino acid azide. The per-N-protected intermediates are conveniently reduced to the corresponding 4-N-alkyl derivatives with diborane. After isolation with column chromatography, the N-protecting groups of both the 4-N-acyl and alkyl derivatives are conveniently removed by photolysis, by, for example, using an ultra violet light and an inert solvent such as ethanol, and the products can be isolated as the free base or as a salt.

Representative 4-N-acyl and alkyl derivatives of des-β-lysyl antibiotic AX-127B-1 include:
4-N-glycyl-2'-N-des-β-lysyl AX-127B-1;
4-N-methyl-2'-N-des-β-lysyl AX-127B-1;
4-N-β-alanyl-2'-N-des-β-lysyl AX-127B-1;
4-N-β-sarcosyl-2'-N-des-β-lysyl AX-127B-1;
4-N-(2-hydroxyethyl)-2'-N-des-β-lysyl AX-127B-1;
4-N-acetyl-2'-N-des-β-lysyl AX-127B-1;
4-N-propionyl-2'-N-des-β-lysyl AX-127B-1;
4-N-(2-hydroxy-4-aminobutyryl)-2'-N-des-β-lysyl-AX-127B-1;
4-N-dimethylamino-2'-N-des-β-lysyl-AX-127B-1;
4-N-iso-propyl-2'-N-des-β-lysyl AX-127B-1;
4-N-n-hexyl-2'-N-des-β-lysyl AX-127B-1;
4-N-seryl-2'-N-des-β-lysyl AX0127B-1; etc.

The present invention includes within its scope pharmaceutical compositions comprising, as an active ingredient, 2'-N-des-β-lysyl-antibiotic AX-127B-1 or a pharmaceutically acceptable salt thereof in association with a pharmaceutically acceptable carrier or diluent. The compounds are administered parenterally (i.e. by intramuscular, intravenous, intraperitoneal or subcutaneous routes of injection) or, to sterilize the gastrointestinal tract, by oral routes of administration, and can be formulated in dosage forms appropriate for each route of administration.

Solid dosage forms for oral administration include capsules, tablets, pills, powders and granules. In such solid dosage forms, the active compound is admixed with at least one inert carrier or diluent such as sucrose, lactose or starch. Such dosage forms can also comprise buffering agents. Tablets and pills can additionally be prepared with enteric coatings.

Liquid dosage forms for oral administration include pharmaceutically acceptable emulsions, solutions, suspensions, syrups and elixirs, containing intert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqeuous or non-aqueous solutions, suspensions or emulsions. Examples of non-aqueous solvents or vehicles are propylene glycol, polyethylene glycol, vegetable oils such as olive oil, and injectable organic esters such as ethyl oleate. Such dosage forms may also contain adjuvants such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. The can also be manufactured in the form of sterile solid compositions which can be dissolved in sterile water, or some other sterile injectible medium immediately before use.

The dosage of the active ingredient in the composition may be varied to accommodate pediatric dosages, adult dosages, etc. However, it is necessary that the amount of active ingredient shall be such that a suitable dosage form is obtained.

The following examples further illustrate the present invention.

EXAMPLE 4

Tablets weighing 500 mg and having the following composition are formulated:

| Ingredient | Mg |
| --- | --- |
| 2'-N-des-β-lysyl-antibiotic AX-127B-1 | 250 |
| Starch | 200 |
| Colloidal silica | 44 |
| Magnesium stearate | 6 |

EXAMPLE 5

Sterile 25 ml ampules are prepared containing 20 mg/ml of 2'-N-des-β-lysyl-antibiotic AX-127B-1 hydrochloride, 0.1 percent sodium bisulfate, 0.7 percent sodium chloride, 0.5 percent chlorobutanol and water q.s.

I claim:

1. 2'-N-Des-β-lysyl-antibiotic AX-127B-1 or a pharmaceutically acceptable salt thereof.

2. A 2'-N-Des-β-lysyl-4-N-acyl or alkyl derivative of antibiotic AX-127B-1 represented by the formula:

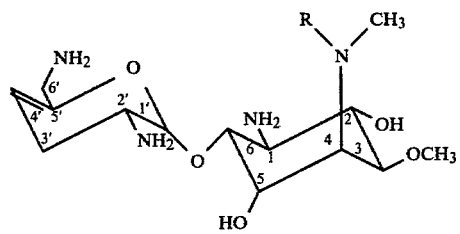

wherein R is acyl, aminoacyl, diaminoacyl excluding β-lysyl, N-loweralkylaminoacyl, N,N-diloweralkylaminoacyl, hydroxy-substituted aminoacyl, loweralkyl, aminoloweralkyl, diaminoloweralkyl, hydroxyloweralkyl, N-loweralkylaminoloweralkyl, N,N-diloweralkylaminoloweralkyl, N-loweralkylaminohydroxyloweralkyl and N,N-diloweralkylaminohydroxyloweralkyl and the pharmaceutically acceptable salts thereof.

3. A compound of claim 2: 4-N-glycol-2'-N-des-β-lysyl AX-127B-1 or a pharmaceutically acceptable salt thereof.

4. A compound of claim 2: 4-N-methyl-2'-N-des-β-lysyl AX-127B-1 or a pharmaceutically acceptable salt thereof.

5. A compound of claim 2: 4-N-β-alanyl-2'-N-des-β-lysyl AX-127B-1 or a pharmaceutically acceptable salt thereof.

6. A compound of claim 2: 4-N-β-sarcosyl-2'-N-des-β-lysyl AX-127B-1 or a pharmaceutically acceptable salt thereof.

7. A compound of claim 2: 4-N-(2-hydroxyethyl)-2'-N-des-β-lysyl AX-127B-1 or a pharmaceutically acceptable salt thereof.

8. A compound of claim 2: 4-N-acetyl-2'-N-des-β-lysyl AX-127B-1 or a pharmaceutically acceptable salt thereof.

9. A compound of claim 2: 4-N-propionyl-2'-N-des-β-lysyl AX-127B-1 or a pharmaceutically acceptable salt thereof.

10. A compound of claim 2: 4-N-(2-hydroxy-4-aminobutyryl)-2'-N-des-β-lysyl AX-127B-1 or a pharmaceutically acceptable salt thereof.

11. A compound of claim 2: 4-N-dimethylamino-2'-N-des-β-lysyl AX-127B-1 or a pharmaceutically acceptable salt thereof.

12. A compound of claim 2: 4-N-iso-propyl-2'-N-des-β-lysyl AX-127B-1 or a pharmaceutically acceptable salt thereof.

13. A compound of claim 2: 4-N-n-hexyl-2'-N-des-β-lysyl AX-127B-1 or a pharmaceutically acceptable salt thereof.

14. A compound of claim 2: 4-N-seryl-2'-N-des-β-lysyl AX-127B-1 or a pharmaceutically acceptable salt thereof.

15. A pharmaceutical composition comprising an antibacterially effective amount of a compound of claim 1 and a pharmaceutically acceptable carrier or diluent.

* * * * *

UNITED STATES PATENT AND TRADEMARK OFFICE
CERTIFICATE OF CORRECTION

PATENT NO. : 4,338,307
DATED : July 6, 1982
INVENTOR(S) : Paul Kurath

It is certified that error appears in the above—identified patent and that said Letters Patent is hereby corrected as shown below:

In column 7, line 10, please delete "glycol", and insert

. . . glycyl . . .

Signed and Sealed this

Twenty-second Day of March 1983

[SEAL]

Attest:

GERALD J. MOSSINGHOFF

Attesting Officer    Commissioner of Patents and Trademarks